US00PP31102P2

(12) United States Plant Patent
Egger

(10) Patent No.: US PP31,102 P2
(45) Date of Patent: Nov. 19, 2019

(54) ***PHYGELIUS* PLANT NAMED 'TNPHYCO'**

(50) Latin Name: ***Phygelius* x *rectus***
Varietal Denomination: TNPHYCO

(71) Applicant: Terra Nova Nurseries, Inc., Canby, OR (US)

(72) Inventor: Janet N. Egger, Seattle, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 16/350,833

(22) Filed: Jan. 18, 2019

(51) Int. Cl.
*A01H 5/02* (2018.01)
*A01H 6/00* (2018.01)

(52) U.S. Cl.
USPC ..... Plt./468

(58) Field of Classification Search
USPC ..... Plt./263.1, 468
See application file for complete search history.

*Primary Examiner* — Susan McCormick Ewoldt
*Assistant Examiner* — Karen M Redden
(74) *Attorney, Agent, or Firm* — Klarquist Sparkman, LLP

(57) ABSTRACT

A new and distinct cultivar of *Phygelius* plant characterized by medium size dark orange flowers, a long bloom time, an upright, well branched habit, with multiple crowns from the base, clean-looking, deep green foliage, and excellent vigor.

1 Drawing Sheet

Botanical denomination: *Phygelius* x *rectus*.
Variety designation: 'TNPHYCO'.

BACKGROUND OF THE INVENTION

The present invention relates to a new and distinct cultivar of *Phygelius*, given the name, 'TNPHYCO'. *Phygelius* is in the family Scrophulariaceae. *Phygelius* x *rectus* 'TNPHYCO' is from a controlled cross using *Phygelius* '70-1', a proprietary, unnamed plant as the seed parent, and *Phygelius* '72-1', a proprietary, unnamed plant as the pollen parent. It was part of a controlled breeding program to produce upright, compact habits with high flower count. This cultivar was selected for medium size, dark orange flowers, high flower count, an upright and well branched habit, multiple crowns from the base and extended bloom time, and clean-looking, deep green foliage.

The Trade designation of the new cultivar is COLORBURST™ Orange.

Compared to the seed parent, *Phygelius* '70-1', the new cultivar has brighter orange flowers, better upright habit, and better rebloom.

Compared to the pollen parent, *Phygelius* '72-1', the new cultivar has a more upright habit and improved rebloom.

Compared to *Phygelius* x *rectus* 'Festive Orange', an unpatented cultivar, the new cultivar is more upright with darker red-orange flowers Compared to *Phygelius* 'Funfare Orange', an unpatented cultivar, the new cultivar has dark red-orange flowers rather than deep salmon.

*Phygelius* 'TNPHYCO' is uniquely distinguished by its:

1. medium size dark orange flowers,
2. high flower count,
3. long bloom time,
4. upright, well branched habit, with multiple crowns from the base,
5. clean-looking, deep green foliage, and
6. excellent vigor.

The new variety has been reproduced only by asexual propagation (cuttings and micropropagation). Each of the progeny exhibits identical characteristics to the original plant. Asexual propagation by cuttings and micropropagation using terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
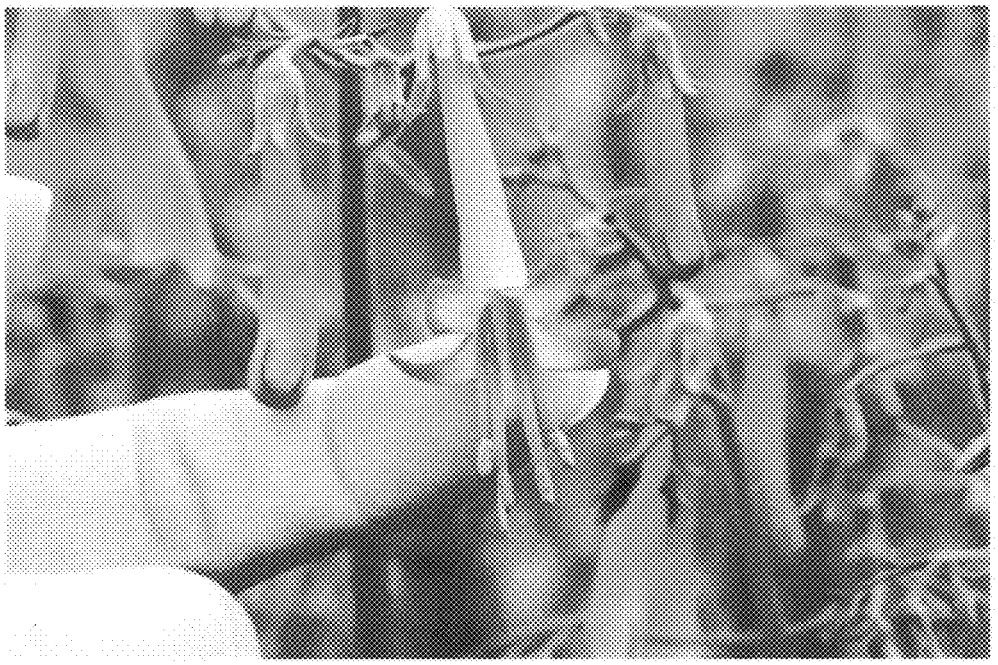
FIG. 1 shows a close up of a flower on a three-year-old *Phygelius* 'TNPHYCO' in the summer in Canby, Oreg.
Figure 2:
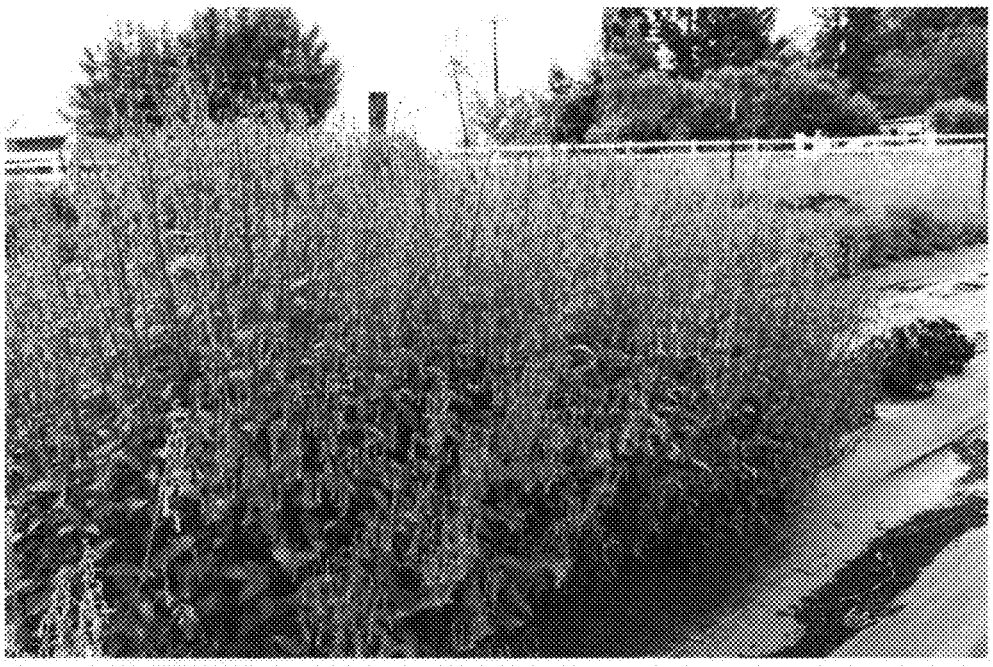
FIG. 2 shows a three-year-old *Phygelius* 'TNPHYCO' in bloom growing in full sun in the garden in June in Canby, Oreg.

The following is a detailed description of the new *Phygelius* cultivar based on observations of a 3-year-old specimen grown outside in a trial garden in Canby, Oreg. in July. The color descriptions are all based on *The Royal Horticultural Society Colour Chart*, $5^{th}$ edition, 2007, except where general color terms of ordinary dictionary significance are used.

Plant:

*Type*.—Semi-evergreen subshrub.
*Form*.—Upright, branching.
*Cold hardiness*.—USDA Zone 7-10.
*Size*.—Grows to 115 cm tall and 87 cm wide.
*Vigor*.—Excellent.
*Stem number*.—25 main stems from the crown.

*Stem*.—Upright, grows to 80 cm long and 11 cm wide (at the base), glabrous, internodes grow to 11 cm long, Grey Brown 199A.

*Rooting*.—Plants root easily from stem cuttings.

Leaf:

*Type*.—Simple

*Arrangement*.—Opposite.

*Shape*.—Ovate lanceolate.

*Venation*.—Pinnate.

*Margins*.—Serrate.

*Apex*.—Acute.

*Base*.—Cuneate.

*Blade size*.—Grows to 7.5 cm long and 3.6 cm wide.

*Petiole*.—Grows to 2.4 cm long and 0.3 cm wide, closest to Green 138A.

*Surface texture*.—Glabrous on both sides.

*Leaf color*.—Topside closest to Green N137A with main vein at base Green 137C, bottom side Green 138B.

Inflorescence:

*Type*.—One-sided, pyramidal panicle with pendulous flowers.

*Number of flowers per inflorescence*.—About 120.

*Size of inflorescence*.—Grows to 35 cm long and 10 cm wide.

*Peduncle*.—Grows to 3 cm long and 0.5 cm wide, glabrous, closest to Greyed Orange 177B.

*Pedicel*.—Grows to 1.5 cm long and 1 mm wide, glabrous, closest to Greyed Orange 177B.

*Bloom period*.—Mid June to frost in Canby, Oreg.

Flower bud:

*Size*.—4.2 cm long and 0.8 cm wide at the widest area.

*Description*.—Tubular, pendulous.

*Color*.—Closest to Orange Red 32B.

Flower:

*Type*.—Zygomorphic, perfect.

*Shape*.—Tubular.

*Size*.—Grows to 5 cm long and 1.8 cm wide.

*Corolla description*.—Grows to 4.9 cm long and 2 cm wide; both sides glabrous; tube 3.8 cm long, swollen to 5 cm wide on bottom side for 0.5 cm under the calyx then narrows to 0.4 cm wide and expanding to 1.1 cm wide below the lobes; 5 lobes, reflexed, oblong, tips obtuse, margins entire, lobes 0.7 cm long and 0.5 cm wide; outside closest to Orange Red 34C, inside Orange Red 34A on lobes for 2 mm, Yellow 13C ring extending into tube.

*Calyx description*.—7 mm deep and 8 mm wide, 5 spreading, slightly reflexed lobes cut almost to the base, glabrous inside and out, each lobe lanceolate in shape, 5 mm long and to 0.2 cm wide, margins entire, tip acute, closest to Greyed Yellow 162B.

*Pistil description*.—1, 5.4 cm long, ovary 0.5 cm long and 0.3 cm wide, closest to Greyed Yellow 160A; style 4.6 cm long and less than 1 mm wide, Greyed Yellow 160D; stigma 1 mm Greyed Red 181D.

*Stamen description*.—4, filaments: two short 1.5 cm long and two long 2 cm and 1 mm wide, Greyed Purple 187A, anthers 0.3 cm long and 0.2 cm wide, Brown N200A.

*Pollen*.—Low, Grey Brown N199A.

*Fragrance*.—None.

*Lastingness*.—A flower lasts about a week on a plant.

Fruit:

*Type*.—Capsule, curved.

*Fertility*.—Poor.

*Size*.—1 cm deep and 5 mm wide.

*Color*.—Brown 200D.

Seed: None seen.

Pests and diseases: Plants of the new *Phygelius* have not been observed to be resistant to pathogens and pests common to *Phygelius*.

I claim:

1. A new and distinct cultivar of *Phygelius* plant substantially as shown and described.

* * * * *